[19] United States Patent
Spona et al.

[11] 3,987,159
[45] Oct. 19, 1976

[54] STABLE SENSITIZED ERYTHROCYTES AND PREPARATION MEANS

[75] Inventors: Jürgen Spona, Vienna, Austria; Michael Töpert, Berlin, Germany

[73] Assignee: Schering Aktiengesellschaft, Berlin & Bergkamen, Germany

[22] Filed: Mar. 1, 1974

[21] Appl. No.: 447,205

[30] Foreign Application Priority Data
Mar. 2, 1973 Germany............................ 2310964

[52] U.S. Cl.................................. 424/12; 195/63; 195/103.5 R; 424/3; 424/8; 424/11; 424/13; 424/75
[51] Int. Cl.² ................ A61K 35/12; G01N 1/00; G01N 31/00; G01N 33/16
[58] Field of Search .............. 424/3, 11, 12, 13, 75; 23/230 B; 195/103.5; 195/63, 68

[56] References Cited
UNITED STATES PATENTS
3,057,775  10/1962  Rendon................................ 424/3
3,096,250  7/1963  Ingraham.............................. 424/12
3,548,051  12/1970  Dingwall............................... 424/3
3,553,310  1/1971  Csizmas............................... 424/12 X FOREIGN PATENTS OR APPLICATIONS
2,132,499  1/1972  Germany.............................. 424/12

OTHER PUBLICATIONS
Onkelinx, Immunology, vol. 16, 1969, pp. 35–43.

Primary Examiner—James O. Thomas, Jr.
Assistant Examiner—A. P. Fagelson
Attorney, Agent, or Firm—Millen, Raptes & White

[57] ABSTRACT

Stable preparations of sensitized erythrocytes are provided by simultaneously admixing washed erythrocytes in a buffered aqueous solution of glutaraldehyde, antigen or antigen-protein conjugate and formaldehyde. After washing, the separated sensitized erythrocytes can be lyophilized and thereby become stable at room temperature.

15 Claims, No Drawings

STABLE SENSITIZED ERYTHROCYTES AND PREPARATION MEANS

BACKGROUND OF THE INVENTION

This invention relates to a process for the production of stable, lyophilized erythrocyte preparations sensitized by coating with an antigen or antigen-protein conjugate, respectively which are useful for the quantitative determination of the antigen, e.g., in hemagglutination reactions. More particularly, the process of this invention is characterized by combining erythrocytes, antigen, glutaraldehyde and formaldehyde in the presence of a buffer solution, allowing the components to simultaneously act on each other under continuous agitation, washing and subsequently lyophilizing the thus-coated erythrocytes. This invention furthermore relates to the erythrocyte preparation obtained according to this process.

Red blood cells or erythrocytes (generally from sheep) are widely used in immunochemical diagnostic techniques, particularly sensitized erythrocytes to which an immunologically or biochemically active group has been directly or indirectly bonded for hemagglutination testing. In virtually all diagnostic procedures employing sensitized erythrocytes, the freshness of the erythrocytes themselves as well as of the sensitized preparation has been a key factor necessary to obtain accurate and reproducible test results. While the preparation of sensitized erythrocyte complexes requires materials, time and skills not always available in clinical laboratories, the instability of such preparations has severely limited commercial exploitation of the potential broad use for such materials manufactured on a large scale.

The problems encountered in freezing red blood cells are compounded when using sensitized erythrocytes. Not only must cell wall rupture be minimized to the greatest extent possible, but this must be done without adversely affecting the sensitization coating as well.

Suitable antigens known to be useful in sensitizing erythrocytes include but are not limited to the proteohormones, e.g., corpus luteam hormone (LH, luteinizing hormone), follicle-stimulating hormone (FSH), growth hormone (STH, somatotropic hormone), prolactin, insulin, etc., and in particular human chorionic gonadotrophin (HCG) and human placenta lactogen (HPL). As these latter two proteohormones in particular are found in the blood and urine of pregnant women, the quantitative determination thereof is of great importance in the detection and monitoring of a pregnancy. L. Wide and C. A. Gemzell developed pregnancy reactions with antigen-bound erythrocytes and antiserum described in Acta Endocrinol. 35: 261 (1960). These reactions are useful both for monitoring pregnancies and for the early determination of pathological manifestations.

Enzymes are also suitable as antigens for sensitizing erythrocytes, e.g., glutamate-oxalacetate transaminase (GOT), glutamic pyruvic transaminase (GPT), lactate dehydrogenase, etc.

Useful antigens also include a great variety of different substances, the detection of which in the blood, urine or other body fluids by techniques employing sensitized erythrocytes is of clinical interest. Among these substances are peptide hormones, e.g., oxytocin and angiotensin; steroid hormones, e.g., testosterone, estradiol, hydrocortisone, etc.; medicinal agents and drugs, e.g., fluocortolone, lysergic acid diethylamide, etc. It will be readily apparent that rapid quantitative determinations of all these substances for diagnostic purposes and for control or screening examinations are of great value to clinicians.

Substances having a low molecular weight can be bound to the erythrocytes directly, if they possess functional groups suitable for cross-linking, e.g., amino groups, or after the introduction of such groups, for use in the process of this invention. Since this binding process often causes damage to the erythrocytes, they can advantageously be first linked with a high-molecular weight "carrier" protein, which serves to protect the substance of interest from causing excessive damage to the erythrocytes during coupling. The linking process resides in the formation of a chemical bond between the antigen and the carrier protein to form an antigen-protein conjugate, which is then coupled to the erythrocytes. Suitable carrier proteins are known and include but are not limited to albumins of various sources, e.g., bovine serum albumin and rabbit serum albumin; globulins of various species, e.g., bovine-α-globulin (BGG) and equine-α-globulin; synthetic polypeptides, e.g., poly-DL-Ala-poly-(Glu, Try)-poly-Lys and poly-(Glu,Tyr)-poly-DL-Ala-poly-Lys; etc.

Detection reactions with antigen-coated erythrocytes, or erythrocytes coated with antigen-protein conjugate, and antiserum are effected, e.g., by direct or indirect hemagglutination reactions analogously to the pregnancy determining and monitoring reactions, described above, as is known to those skilled in the art e.g., by direct and indirect hemagglutination (HA), hemagglutination inhibition (HAI), etc.

Antigen-coated erythrocytes have been described, e.g., see L. Wide, C. A. Gemzell, Acta Endocrinol. 35(1960) 261. However, the coated erythrocytes are unstable. Several attempts have been made to overcome this disadvantage by the use of coupling and stabilizing agents in the production of the erythrocyte preparations.

Thus, many bivalent reagents have been proposed as coupling agents between antigens and erythrocytes, e.g., bis-diazotized benzidines described in Int. Arch. Allergy 13:1 (1958); 1,3-difluoro-4,6-dinitrobenzene described in Immunology 4:49 (1961); toluene-2,4-diisocyanates described in Immunochemistry 1:43 (1964); 1-ethyl-3-(3-dimethylaminopropyl)carbodiimide described in J. Immunol. 97:791 (1966); glutaraldehyde described in Brit. J. Haemat. 7:299 (1961); etc. Since even the coupling-coated erythrocytes are still readily susceptible to decomposition, the erythrocytes have further been hardened by treating with formaldehyde prior to coating, e.g., using the procedure described in Proc. Soc. Exp. Biol. (N.Y.) 99:452 (1958). The processes are thereby made complicated and expensive and, due to the numerous stages employed, do not always yield reproducible results.

In DOS (German Unexamined Laid-Open Application) 2,132,499, a serum-diagnostic composition of chorionic gonodotrophin bound to red blood cells by means of glutaraldehyde as the coupling agent is described. In order to increase the stability of the sensitized erythrocytes, these blood cells are aftertreated with glutaraldehyde or formaldehyde. The sensitized blood cells are obtained in the form of a suspension in a buffer solution. The aftertreatment with glutaraldehyde or formaldehyde renders the process expensive; furthermore, the HCG-sensitized red blood cells can be satisfactorily preserved in the suspension only if the latter is stored under refrigeration at 2°–8° C.

OBJECTS OF THE INVENTION

Accordingly, it is a general object of this invention to provide an economical process for preparing sensitized erythrocytes useful in immunochemical techniques.

Another object of this invention is to provide a process for preparing sensitized erythrocyte preparations having improved stability and extended shelf life.

A further object of this invention is to provide sensitized erythrocyte preparations which are stable at room temperature.

An additional object of this invention is to provide a process for preparing sensitized erythrocyte preparations having improved consistency of activity from batch to batch.

Upon further study of the specification and appended claims, further objects and advantages of this invention will become apparent to those skilled in the art.

SUMMARY OF THE INVENTION

Briefly, the above and other objects are attained in one aspect of the present invention by providing a process for the preparation of hemagglutination sensitized, antigen-coated erythrocytes suitable for use in immunochemical diagnostic techniques, which comprises:

a. admixing a suspension of washed erythrocytes in an aqueous solution containing an erythrocyte-coupling amount of glutaraldehyde, a coupled-glutaraldehyde-complexing amount of an erythrocyte-sensitizing antigen or antigen-protein conjugate and an erythrocyte-hardening amount of formaldehyde, under incubation conditions at a pH of 5.5 – 8.5 for a period of time sufficient to form erythrocytes sensitized to hemagglutination by the coupling of said antigen or antigen-protein conjugate thereto; and b. recovering said sensitized erythrocytes from said admixture.

DETAILED DISCUSSION

It has now been found that a stable, lyophilizable antigen or antigen-protein-conjugate-coated erythrocyte preparation can be obtained by allowing the erythrocytes, the antigen, glutaraldehyde and formaldehyde to interact simultaneously on one another in a buffer solution. After the thus-coated erythrocytes have been washed, the preparation can be obtained in the solid form by lyophilizing. The lyophilized erythrocyte preparation is stable at room temperature. The process can be conducted in a single reaction vessel and can be utilized with a wide variety of different antigens and/or antigen-protein conjugates.

In accordance with a preferred embodiment, the erythrocytes are coated in an aqueous solution maintained at a pH of 5.5 to 8.5, preferably of about 7.0 to 7.2. Suitable buffers can be used; these are well known in the art and include but are not limited to phosphate buffers, borate buffers, tris buffers, etc. The required buffer strength must be sufficient to maintain the pH in the range of 5.5 to 8.5 throughout the reaction.

Suitable concentrations of the various reactants, in vol. %, are approximately:

| USEFUL | PREFERRED | |
|---|---|---|
| 4 – 12 % | 6 – 10 % | erythrocytes |
| 0.2 – 2 % | 0.4 – 1 % | glutaraldehyde |
| 0.6 – 6 % | 1 – 4 % | formaldehyde |
| 0.01–0.25 % | 0.02–0.125% | antigen or antigen-protein conjugate (wt./vol., as protein) |
| isotonic | 0.08–0.3 mNaCl | ionic strength |

The required reaction time depends on the stable incubation or reaction temperature employed, which can be varied from the freezing point of the admixture or its components to the denaturation temperature of the protein or erythrocytes therein. Incubation periods of about 1 and 12 hours and temperatures of about 5°–45° C are generally required. At the preferred incubation temperature of about 37° C, the reaction is usually terminated after about 4 hours.

The coated erythrocytes are washed in the buffer solution until free of unreacted material, and can then be suspended for freeze-drying in a fresh buffer solution having a pH of 5–8, preferably 6.2 – 6.5. It is advantageous to provide that the second buffer solution additionally contains 0.005 – 0.2 % gelatin, 0.1 – 2 % glycine, and 0.05 – 0.5 % polyvinylpyrrolidone, e.g., BASF "Kollidon". The latter and gelatin effect an improved re-suspendability of the erythrocytes, while glycine protects the preparation from damage during freeze-drying. The freeze-dried preparation can be conveniently stored, e.g., in hermetically sealed ampoules under a nitrogen atmosphere.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise specified, all parts and percentages are weight per volume.

EXAMPLE 1

Production of an HPL-Coated Lyophilized, Stable Erythrocyte Preparation

Starting Materials:
1. Sheep erythrocytes (obtained from Behringwerke, Marburg, West Germany)
2. HPL, human placenta lactogen (95% pure, from Nutritional Biochemicals Corp., Ohio)
3. Aqueous glutaraldehyde solution, 25% (g/g)
4. Aqueous formaldehyde solution, 35% (g/g)
5. Phosphate buffer I, consisting of 0.075 m $NaH_2PO_4$ + 0.45% NaCl, pH 7.2, 0.01% thimerosal ("Merthiolate")
6. Phosphate buffer II, consisting of 0.019 m $NaH_2PO_4$ + 0.11% NaCl, pH 6.4, 0.31% pulverized gelatin, 0.56% glycine (pro analysis), 0.125% polyvinylpyrrolidone ("Kollidon 25") and 0.0025% thimerosal ("Merthiolate")

Pretreatment:

The sheep erythrocytes are washed twice with a two-fold volume of physiological saline solution and once with phosphate buffer I. The washing liquid is separated after each wash by centrifuging the suspension at 750 g.'s in a refrigerated centrifuge at 4° C. After washing, the erythrocytes are brought to an 8% suspension in phosphate buffer I. The percentages for the erythrocyte suspensions refer to hematocrit values determined after centrifuging at 100 g.'s for 10 minutes.

Treatment:

To 1 part by volume of the washed 8% erythrocyte suspension in phosphate buffer I are added 0.5 part by volume of a 0.66% glutaraldehyde solution in phosphate buffer I, 0.5 part by volume of a 2% formaldehyde solution in phosphate buffer I, and 1 part by volume of a 0.05% HPL solution in phosphate buffer I.

The resultant admixture is incubated for 4 hours at 37° C in an obliquely positioned round vessel which rotates slowly about its own axis. The incubated erythrocytes are then washed three times in phosphate buffer I, and separated at 250 g.'s in the cooled centrifuge.

The thus-coated erythrocytes are re-suspended in phosphate buffer II as a 0.75% suspension, dispersed in 2 ml aliquots into ampoules, frozen by immersion of the ampoules into a mixture of methanol and dry ice, and freeze-dried under dry nitrogen at a pressure of 0.01–0.1 mm. Hg. absolute. The freeze-dried erythrocytes are subjected to a post drying step for about 24 hours in a desiccator over $P_2O_5$ before the glass ampoules are sealed by melting. The freeze-dryer and the desiccator are both purged and maintained under an atmosphere of dry nitrogen, which is also used to replenish the vacuum following lyophilization.

The freeze-dried erythrocyte preparation produced in this manner exhibits about 95–100% of the activity of the fresh preparation immediately after lyophilization (as determined by hemagglutination) and is stable at room temperature for 6 – 12 months and at 37° C for 1 – 3 months.

EXAMPLE 2

Production of an HCG-Coated Lyophilized, Stable Erythrocyte Preparation

Following the protocol of Example 1, but with the use of HCG, human chorionic gonadotrophin (5000 IU/mg.) in place of HPL, analogous results are obtained. The lyophilized preparation has 95–100% of the activity of the freshly prepared complex (as determined by hemagglutination), and is stable at room temperature for 6 – 12 months and at 37° C for 1 – 3 months.

EXAMPLE 3

Production of a $DNP_3$-BGG-Coated Lyophilized, Stable Erythrocyte Preparation

Following the protocol of Example 1, but with the use of $DNP_3$-BGG (dinitrophenyl-bovine-γ-globulin) in place of HPL, analogous results are obtained. The lyophilized preparation has 95–100% of the activity of the freshly prepared complex (as determined by hemagglutination), and is stable at room temperature for 6 – 12 months and at 37° C for 1 – 3 months.

EXAMPLE 4

Production of a $Fluocortolone_{40}$-BGG-Coated Lyophilized, Stable Erythrocyte Preparation Following the protocol of Example 1, but with the use of fluocortolone-BGG, $fluocortolone_{40}$-bovine-γ-globulin, in place of HPL, analogous results are obtained. The lyophilized preparation has 95–100% of the activity of the freshly prepared complex (as determined by hemagglutination), and is stable at room temperature for 6 – 12 months and at 37° C for 1 – 3 months.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of sensitized, antigen-coated erythrocytes suitable for use in immunochemical hemagglutination diagnostic techniques by admixing a reaction mixture containing a suspension of washed erythrocytes in an aqueous solution containing an erythrocyte-sensitizing amount of an antigen or antigen-carrier protein conjugate and a coupling amount of glutaraldehyde under erythrocyte-sensitizing incubation conditions for a period of time sufficient to form erythrocytes sensitized by the coupling thereto of said antigen or antigen-carrier protein conjugate thereof, the improvement comprising simultaneously reacting said admixture with an erythrocyte-hardening amount of formaldehyde at a temperature of about 5°–45° C. for about 1–12 hours while maintaining the pH of the resultant admixture at 5.5–8.5 to form sensitized, antigen-coated erythrocytes capable of being lyophilized to form a preparation exhibiting 95–100% of the hemagglutination activity of the fresh preparation and which is stable for 6–12 months at room temperature.

2. The process of claim 1, wherein said aqueous solution is buffered to a pH of about 7.0–7.2.

3. The process of claim 1, wherein said temperature is about 37° C.

4. The process of claim 2, wherein said temperature is about 37° C. and the incubation time is about 4 hours.

5. The process of claim 1, wherein said antigen is a hormone or an enzyme.

6. The process of claim 5, wherein said antigen is a proteohormone.

7. The process of claim 6, wherein said proteohormone is human chorionic gonadotropin or human placenta lactogen.

8. The process of claim 1, wherein

4–12% washed erythrocytes;
    0.2–2% glutaraldehyde;
    0.6–6% formaldehyde; and
    0.01–0.25% antigen or antigen-carrier protein conjugate are admixed.

9. The process of claim 1, further comprising lyophilizing said sensitized erythrocytes.

10. The process of claim 9, wherein, prior to lyophilizing, the sensitized erythrocytes are re-suspended in a buffer solution having a pH of 5–8 and which contains sufficient glycine to protect the sensitized erythrocytes from damage during lyophilization.

11. The process of claim 10, wherein said buffer further comprises sufficient polyvinylpyrrolidone and gelatin to improve re-suspendability of the sensitized erythrocytes.

12. Sensitized, antigen-coated erythrocytes suitable for use in immunochemical hemagglutination diagnostic techniques prepared by the process of claim 1.

13. The product of claim 12, wherein said erythrocytes are sheep erythrocytes.

14. The product of claim 13, lyophilized and hermetically sealed in an inert atmosphere.

15. The product of claim 14, wherein the antigen or antigen-carrier protein conjugate is selected from the group consisting of human placenta lactogen, human chorionic gonadotrophin, dinitrophenyl-bovine gamma globulin and fluocortolone-bovine gamma globulin.

* * * * *